(12) United States Patent
Vitello et al.

(10) Patent No.: US 11,541,180 B1
(45) Date of Patent: Jan. 3, 2023

(54) CLOSURE ASSEMBLY HAVING A SNAP-FIT CONSTRUCTION

(71) Applicants: Patrick Vitello, Pompano Beach, FL (US); Timothy Brandon Hunt, Hollywood, FL (US)

(72) Inventors: Patrick Vitello, Pompano Beach, FL (US); Timothy Brandon Hunt, Hollywood, FL (US)

( * ) Notice: Subject to any disclaimer, the term of this patent is extended or adjusted under 35 U.S.C. 154(b) by 393 days.

(21) Appl. No.: 16/229,354

(22) Filed: Dec. 21, 2018

Related U.S. Application Data (60) Provisional application No. 62/609,035, filed on Dec. 21, 2017.

(51) Int. Cl.
*A61M 5/50* (2006.01)
*A61M 5/31* (2006.01)

(52) U.S. Cl.
CPC ............ *A61M 5/31* (2013.01); *A61M 5/5086* (2013.01); *A61M 2005/312* (2013.01); *A61M 2005/3104* (2013.01)

(58) Field of Classification Search
CPC .................. A61M 5/50; A61M 5/5086; A61M 2005/312; A61M 2005/3104; B65D 51/20; B65D 41/3428; B65D 2401/00; B65D 2401/20; B65D 2401/50
See application file for complete search history.

(56) References Cited

U.S. PATENT DOCUMENTS

| | | |
|---|---|---|
| 722,943 A | 3/1903 | Chappell |
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |

(Continued)

FOREIGN PATENT DOCUMENTS

| | | | | |
|---|---|---|---|---|
| EP | 0148116 A | | 7/1985 | |
| GB | 486367 A | * | 6/1938 | ......... B65D 43/0256 |

(Continued)

OTHER PUBLICATIONS

Arai Tsugio, Pilfering Proof Cap, Jan. 1, 1996.

*Primary Examiner* — Rebecca E Eisenberg
*Assistant Examiner* — Anna E Goldberg-Richmeier
(74) *Attorney, Agent, or Firm* — Malloy & Malloy, PL; Jennie S. Malloy; Peter A. Matos (57) ABSTRACT

A closure assembly for a medical device, preferably in the form of a tamper evident closure, having an outer sleeve including an open end and a closed end. A tip cap includes a flow restrictor disposed within the sleeve in accessible relation by the medical device through the open end. An indicator member is removably connected to the tip cap within the sleeve and a retainer member is connected to an interior of the sleeve in an interruptive, disconnecting relation to the indicator member by a snap-fit connection. The indicator member is captured within said hollow interior upon removal of said tip cap from the sleeve through the open end. An end cap may be attached to the sleeve, to define a closed end thereof, by a snap-fit connection similar to, but distinguishable from, the snap-fit connection between the retainer member and the interior of the sleeve.

17 Claims, 9 Drawing Sheets

(56) References Cited

U.S. PATENT DOCUMENTS

| | | |
|---|---|---|
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,489,268 A | 1/1970 | Meierhoefer |
| 3,368,673 A | 3/1971 | Cowley |
| 3,574,306 A | 4/1971 | Alden |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| 5,057,093 A | 10/1991 | Clegg et al. |
| D323,392 S | 1/1992 | Byrne |
| 5,085,332 A | 2/1992 | Gettig et al. |
| 5,090,564 A | 2/1992 | Chimienti |
| 5,135,496 A | 8/1992 | Vetter et al. |
| 5,163,922 A | 11/1992 | McElveen, Jr. et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,662,233 A | 9/1997 | Reid |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Lift et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsais |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |

(56) References Cited

U.S. PATENT DOCUMENTS

| | | |
|---|---|---|
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 * | 8/2016 | Vitello ............... A61M 5/5086 |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,478,262 B2 | 11/2019 | Niese et al. |
| 10,758,684 B1 | 9/2020 | Vitello et al. |
| 10,773,067 B2 | 9/2020 | Davis et al. |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 11,426,328 B1 | 8/2022 | Ollmann et al. |
| 11,471,610 B1 | 10/2022 | Banik et al. |
| 2001/0003150 A1 | 6/2001 | Imbert |
| 2001/0034506 A1 | 10/2001 | Hirschman et al. |
| 2001/0056258 A1 | 12/2001 | Evans |

(56) References Cited

U.S. PATENT DOCUMENTS

| | | | |
|---|---|---|---|
| 2002/0007147 A1* | 1/2002 | Capes | A61M 5/50 604/110 |
| 2002/0023409 A1 | 2/2002 | Py | |
| 2002/0046962 A1 | 4/2002 | Vallans et al. | |
| 2002/0097396 A1 | 7/2002 | Schafer | |
| 2002/0099334 A1 | 7/2002 | Hanson et al. | |
| 2002/0101656 A1 | 8/2002 | Blumenthal et al. | |
| 2002/0104770 A1 | 8/2002 | Shapeton et al. | |
| 2002/0133119 A1 | 9/2002 | Eakins et al. | |
| 2003/0055685 A1 | 3/2003 | Cobb et al. | |
| 2003/0146617 A1 | 8/2003 | Franko, Sr. | |
| 2003/0183547 A1 | 10/2003 | Heyman | |
| 2004/0008123 A1 | 1/2004 | Carrender et al. | |
| 2004/0064095 A1 | 4/2004 | Vitello | |
| 2004/0116858 A1 | 6/2004 | Heinz et al. | |
| 2004/0186437 A1 | 9/2004 | Frenette et al. | |
| 2004/0225258 A1 | 11/2004 | Balestracci | |
| 2005/0146081 A1 | 7/2005 | MacLean et al. | |
| 2005/0148941 A1 | 7/2005 | Farrar et al. | |
| 2005/0209555 A1 | 9/2005 | Middleton et al. | |
| 2006/0084925 A1 | 4/2006 | Ramsahoye | |
| 2006/0089601 A1 | 4/2006 | Dionigi | |
| 2006/0173415 A1 | 8/2006 | Cummins | |
| 2006/0189933 A1 | 8/2006 | Alheidt et al. | |
| 2007/0060898 A1 | 3/2007 | Shaughnessy et al. | |
| 2007/0106234 A1 | 5/2007 | Klein | |
| 2007/0142786 A1 | 6/2007 | Lampropoulos et al. | |
| 2007/0191690 A1 | 8/2007 | Hasse et al. | |
| 2007/0219503 A1 | 9/2007 | Loop et al. | |
| 2007/0257111 A1 | 11/2007 | Ortenzi | |
| 2008/0068178 A1 | 3/2008 | Meyer | |
| 2008/0097310 A1* | 4/2008 | Buehler | A61M 5/50 604/111 |
| 2008/0106388 A1 | 5/2008 | Knight | |
| 2008/0140020 A1 | 6/2008 | Shirley | |
| 2008/0243088 A1 | 10/2008 | Evans | |
| 2008/0303267 A1 | 12/2008 | Schnell et al. | |
| 2008/0306443 A1 | 12/2008 | Neer | |
| 2009/0084804 A1 | 4/2009 | Caspary | |
| 2009/0099552 A1 | 4/2009 | Levy et al. | |
| 2009/0149815 A1 | 6/2009 | Kiel et al. | |
| 2009/0166311 A1 | 7/2009 | Claessens | |
| 2009/0326481 A1 | 12/2009 | Swisher et al. | |
| 2010/0084403 A1 | 4/2010 | Popish et al. | |
| 2010/0126894 A1 | 5/2010 | Koukol et al. | |
| 2010/0179822 A1 | 7/2010 | Reppas | |
| 2010/0228226 A1 | 9/2010 | Nielsen | |
| 2010/0252564 A1 | 10/2010 | Martinez et al. | |
| 2010/0283238 A1 | 11/2010 | Deighan et al. | |
| 2011/0044850 A1 | 2/2011 | Solomon et al. | |
| 2011/0046550 A1 | 2/2011 | Schiller et al. | |
| 2011/0046603 A1 | 2/2011 | Felsovalyi et al. | |
| 2012/0064515 A2 | 3/2012 | Knapp et al. | |
| 2012/0096957 A1 | 4/2012 | Ochman | |
| 2012/0110950 A1 | 5/2012 | Schraudolph | |
| 2013/0018356 A1 | 1/2013 | Prince et al. | |
| 2013/0056130 A1 | 3/2013 | Alpert et al. | |
| 2013/0088354 A1 | 4/2013 | Thomas | |
| 2013/0237949 A1 | 9/2013 | Miller | |
| 2013/0269592 A1 | 10/2013 | Heacock et al. | |
| 2014/0000781 A1 | 1/2014 | Franko, Jr. | |
| 2014/0034536 A1 | 2/2014 | Reinhardt et al. | |
| 2014/0069202 A1 | 3/2014 | Fisk | |
| 2014/0069829 A1 | 3/2014 | Evans | |
| 2014/0135738 A1 | 5/2014 | Panian | |
| 2014/0155868 A1 | 6/2014 | Nelson et al. | |
| 2014/0163465 A1 | 6/2014 | Bartlett, II et al. | |
| 2014/0257843 A1 | 9/2014 | Adler et al. | |
| 2014/0326727 A1 | 11/2014 | Jouin | |
| 2014/0353196 A1 | 12/2014 | Key | |
| 2015/0182686 A1 | 7/2015 | Okihara | |
| 2015/0191633 A1 | 7/2015 | De Boer et al. | |
| 2015/0246185 A1 | 9/2015 | Heinz | |
| 2015/0302232 A1 | 10/2015 | Strassburger et al. | |
| 2015/0305982 A1 | 10/2015 | Bochenko | |
| 2015/0310771 A1 | 10/2015 | Atkinson et al. | |
| 2016/0067422 A1 | 3/2016 | Davis et al. | |
| 2016/0090456 A1 | 3/2016 | Ishimaru et al. | |
| 2016/0136352 A1 | 5/2016 | Smith et al. | |
| 2016/0144119 A1 | 5/2016 | Limaye et al. | |
| 2016/0158110 A1 | 6/2016 | Swisher et al. | |
| 2016/0158449 A1 | 6/2016 | Limaye et al. | |
| 2016/0176550 A1 | 6/2016 | Vitello et al. | |
| 2016/0250420 A1 | 9/2016 | Maritan et al. | |
| 2016/0279032 A1 | 9/2016 | Davis | |
| 2016/0328586 A1 | 11/2016 | Bowden et al. | |
| 2016/0361235 A1 | 12/2016 | Swisher | |
| 2016/0367439 A1 | 12/2016 | Davis et al. | |
| 2017/0007771 A1 | 1/2017 | Duinat et al. | |
| 2017/0014310 A1 | 1/2017 | Hyun et al. | |
| 2017/0124289 A1 | 5/2017 | Hasan et al. | |
| 2017/0173321 A1 | 6/2017 | Davis et al. | |
| 2017/0203086 A1 | 7/2017 | Davis | |
| 2017/0225843 A1 | 8/2017 | Glaser et al. | |
| 2017/0239141 A1 | 8/2017 | Davis et al. | |
| 2017/0319438 A1 | 11/2017 | Davis et al. | |
| 2017/0354792 A1 | 12/2017 | Ward | |
| 2018/0001540 A1 | 1/2018 | Byun | |
| 2018/0014998 A1 | 1/2018 | Yuki et al. | |
| 2018/0078684 A1 | 3/2018 | Peng et al. | |
| 2018/0089593 A1 | 3/2018 | Patel et al. | |
| 2018/0098915 A1 | 4/2018 | Rajagopal et al. | |
| 2019/0388626 A1 | 12/2019 | Okihara | |
| 2022/0008645 A1 | 1/2022 | Ukai et al. | |

FOREIGN PATENT DOCUMENTS

| | | |
|---|---|---|
| JP | 08002544 | 1/1996 |
| KR | 101159987 | 6/2012 |
| WO | WO 2008/000279 | 1/2008 |
| WO | WO 2017086607 | 5/2015 |

\* cited by examiner

CLOSURE ASSEMBLY HAVING A SNAP-FIT CONSTRUCTION

CLAIM OF PRIORITY

The present application is based on and a claim of priority is made under 35 U.S.C. Section 119(e) to a provisional patent application that is in the U.S. Patent and Trademark Office, namely, that having Ser. No. 62/609,035 and a filing date of Dec. 21, 2017, which is incorporated herein by reference in its entirety.

BACKGROUND OF THE INVENTION

Field of the Invention

The present invention is directed to a closure assembly, preferably in the form of a tamper evident closure (TEC), incorporating a snap-fit construction, enabling a snap-fit connection of a plurality of operative components thereof into an operative assembly.

Description of the Related Art

In the medical field, it is a common procedure for authorized medical personnel to order an injection or other type administration of a substance for a patient. It is also a relatively common procedure for a number of administering devices, such as a syringe, to be pre-filled by authorized personnel whether within the hospital or at another filling station. However, such a filling station is typically located in a remote part of the facility, relative to the patient care area, where the injection is to be administered. Because of the remote location of many nurse's stations, relative to a filling station, a fluid or drug loaded syringe or other medical device is frequently given to another person for delivery to a nurse's station for subsequent dosing of the patient. In the case where a prefilled drug in the syringe is very expensive or addictive such as, but not limited to, morphine, there is a danger of tampering, by a person seeking unauthorized access to the prefilled contents of the syringe or medical device.

Accordingly, upon an occurrence of tampering there is a possibility that the prescribed medicine has been replaced by some other, unauthorized substance. By way of an example only, if saline solution were substituted for a dose of morphine or other medication, the result could be extremely serious. Thus, there is a problem of knowing if a sealed, pre-loaded syringe or other administering device has, or has not, been compromised by tampering and/or exposed to contamination so that it is no longer sterile. These and related types of problems have been described in one or more U.S. patents granted to one of the inventor(s) and/or Assignee herein, such as U.S. Pat. No. 5,328,474.

In addition to the administration of drugs, medicine, etc., meaningful protection is required in the use of enteral feeding sets. As commonly recognized in the medical and related professions, the term "enteral" relates to the administration or removal of fluid to or from the gastrointestinal tract. Moreover, enteral connectors and/or fixtures of the type referred to herein relate to medical devices or accessories which are intended for use in enteral applications. Further, small-bore connectors for enteral application may be employed for delivery of enteral nutrition fluid from a fluid source to the patient. Additionally, it is pointed out that enteral feeding sets and extension sets may include a female fixture, wherein the source of fluid flows to the patient initially through the female fixture and to and through a cooperatively structured male enteral fixture.

Also, with regard to administering fluids to a patient by intravenous (IV) infusion, a variety of IV assemblies are used in the treatment of numerous medical conditions. Different types of connectors, such as a "female" connector may be attached to the discharge end or discharge port of an IV bag or like medical device/container. Such an appropriate female connector may be in the form of a female luer connector which at least partially defines, along with a male luer connector, a "luer lock" connector assembly, as is well known in the medical profession. In periods of non-use, it is important to maintain such connectors associated with an IV facility, in a closed and fluid sealed condition in order to maintain sterility and integrity of the IV fluid prior to use.

Therefore, regardless of the known or conventional attempts to provide a fluid restricting closure to protect the contents of preloaded administering devices and/or enteral devices, certain problems still remain in this field of art. Accordingly, there is a need in this area for an improved, closure assembly which provides a secure and reliable fluid restricting or fluid sealing connection to the discharge port, fixture or connector of a medical device of the type set forth herein. If any such improved closure assembly were developed, it would preferably also overcome known disadvantages in the production and/or assembly of conventional closures, including tamper evident closures. However, in order to do so, any such closure assembly would preferably also include a unique construction to help reduce, if not eliminate, the need to utilize conventionally known, time-consuming, costly and overly complicated production techniques associated with the production of closure for medical devices. Also, if any such closure assembly were developed, it should further be capable of use with little or no structural modification to a variety of different connectors, fixtures, administering devices, tip caps, etc. Finally, if any such improved closure assembly were developed, it should also be structurally and operatively reliable, while improving the cost effectiveness associated with the manufacture and assembly thereof.

SUMMARY OF THE INVENTION

The present invention is directed to a closure assembly, preferably in the form of a tamper evident closure (TEC), for a medical device such as, but not limited to, a pre-filled syringe. Inventive features of the closure assembly disclosed herein, and as reflected in one or more illustrated embodiments, include a "snap-fit" construction, which enables the assembly and/or interconnection of the operative components thereof using one or more "snap-fit" connections. By virtue of this snap-fit construction, the formation and assembly of this closure assembly eliminates or significantly reduces commonly used production techniques such as, but not limited to, ultrasonic welding, which is generally considered to be costly, time-consuming and labor intensive.

Accordingly, the one or more preferred embodiments of the closure assembly includes a housing comprising an outer sleeve having an at least partially hollow interior and an open end. The open end is disposed in communicating relation with the hollow interior and may serve as an access opening for the medical device or syringe to which the closure assembly is connected.

A tip cap is structured to be connected in flow sealing or at least flow restricting relation to the discharge port or discharge end of the syringe or other medical device. As such the tip cap includes a flow restrictor which, as set forth in greater detail hereinafter, may assume either a male or female configuration. In addition, the tip cap comprises an indicator member removably connected by at least one and/or a plurality of frangible connectors. In at least one embodiment, the indicator member comprises an indicator ring having an annular configuration disposed in at least partially surrounding relation to a portion of the tip cap. Moreover, the indicator ring is removably connected, by the one or more aforementioned frangible connectors, to an exterior of the tip cap, in substantially surrounding relation to a portion thereof.

In addition, one or more embodiments of the closure assembly include a retainer member disposed within the hollow interior of the outer sleeve in retaining relation to the indicator member. Further, the retainer member is disposed in its retaining position by a snap-fit connection with interior surface portions of the sleeve. As will be explained in greater detail hereinafter, the snap-fit connection between the retainer member and the interior surface of the sleeve is structured to prevent removal of the retainer member from the interior of the sleeve and in some embodiments thereof allow movement, such as rotational movement, of the retainer member within the sleeve.

Additional structural details of the retainer member include a base and at least one, but preferably a plurality, of the connector members attached to the base and extending outwardly therefrom into the aforementioned connection with the interior surface of the sleeve. Further, each of the one or more connector members may include a spring arm having sufficient flexibility to facilitate passage of the retainer member into the interior of the sleeve, through the access opening and into sliding engagement with the interior surface of the sleeve, until it reaches its intended, operative, retaining position. In cooperation therewith, the interior surface of the sleeve includes a radially inward directed projection, as well as a receiving groove contiguous to the inwardly directed projection. The distal end of each of the one or more spring arms is cooperatively structured with the surface projection/receiving groove to interlock therewith, such that removal of the retainer member from the sleeve, back through the access opening is prevented.

As used herein, reference to the prevented removal or non-removal of the retainer member relative to the sleeve is meant to include the resistance of the retainer member from the sleeve when the retainer member is in its normal structural configuration. It is not meant to describe structural situations where the retainer member is purposely or accidentally broken or damaged to the extent of not normally obtaining its retaining position within the sleeve.

The aforementioned snap-fit connection between the retainer member and/or spring arms is at least partially defined by an inward biasing of each of the spring arms as they pass over the interior surface projection. Due to the flexibility of the one or more spring arms, the distal ends will "snap" into a substantially locking engagement with the receiving groove once they pass over the surface projection on the interior of the sleeve. Also, this snap-fit connection does not necessarily represent a fixed attachment of the retainer member and or the one or more spring arms to the interior surface of the sleeve. In contrast, the snap-fit connection may allow a rotational movement the retainer member while in its retaining position relative to the indicator member removably attached to the tip cap. However, as indicated, removal of the retainer member from the interior of the sleeve will be prevented or at least significantly resisted unless the retainer member and or one or more spring arms are broken, damaged or otherwise made inoperative to affect the snap-fit connection.

As emphasized herein, the snap-fit construction of the one or more embodiments of the closure assembly also facilitates the assembly thereof into an operative form, without the use of common production techniques such as, but not limited to ultrasonic welding.

More specifically, the sleeve and the open end as well as adjacent or contiguous portions of the hollow interior are cooperatively dimensioned to receive the tip cap, with the indicator member attached thereto through the open end into the interior of the sleeve. Further, the retainer member is cooperatively dimensioned with the sleeve to facilitate its passage through the open end into the aforementioned snap-fit connection with the interior surface of the sleeve.

When operatively positioned, the retainer member is disposed intermediate the open end and at least the indicator member of the tip cap. Further, when in the snap-fit connection with the interior surface of the sleeve, the one or more spring arms are disposed in interruptive, retaining engagement with the indicator member when it is removably connected to the remainder of the tip cap. In contrast, the base and one or more spring arms of the retainer member define an open interior thereof. This open interior is cooperatively dimensioned with at least the flow restrictor portion of the tip cap to allow its passage there through and out of the interior of the sleeve through the open end.

Therefore, the dimension and configuration of the tip cap is such as to dispose the flow restrictor in accessible relation to the medical device or syringe, to which it is to be attached, through the open end. The intended use of the closure assembly contemplates the discharge port or like structure of the medical device/syringe to pass at least partially through the open end of the sleeve into connected engagement with the flow restrictor. Use of the syringe in terms of accessing the prefilled contents thereof is accomplished by exerting a pulling force on the sleeve and/or syringe, thereby forcing the tip cap, connected to the syringe outwardly through the open interior of the retainer member and through the open end of the sleeve.

Such an outwardly directed force will result in at least a minimal movement of the indicator member with the tip cap, into interruptive, disconnecting engagement with the retainer member. More specifically, the one or more spring arms, will be engaged by the movement of the indicator member outwardly relative to the retainer member, while it is attached to the tip cap. Such engagement will cause a detachment of the indicator member from the flow restrictor and a capturing of the indicator member on the interior of the sleeve. As should be apparent such capturing of the indicator member will occur substantially concurrent to the passage of the flow restrictor and connected syringe outwardly through the open end of the sleeve. A clear indication of tampering or use will be provided by the captured disposition of the indicator member on the interior the sleeve and the removed flow restrictor being attached to the discharge end of the syringe/medical device absent the indicator member.

Yet additional structural and operative features of the closure assembly include the provision of a closed end of the sleeve preferably disposed in opposing relation to the open end thereof. Accordingly, the snap-fit construction of the one or more embodiments of the closure assembly may be further defined by an attachment of an end cap to the sleeve by means of at least one but preferably a plurality of spring fingers formed on the end cap. In this additional structural modification, the sleeve also includes an "apertured construction" cooperatively structured with the one or more spring fingers. As such each of the one or more spring fingers are dimensioned and configured to be disposed within a different one of the plurality of apertures defining the apertured construction. Further, the cooperative structures and configurations of each spring finger with a corresponding aperture will result in a "snap-fit" connection therebetween as the one or more spring fingers penetrate into corresponding apertures formed in the sleeve.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying Figures, the present invention is directed to a closure assembly generally indicated as 10, which is preferably in the form of a tamper evident closure (TEC). Inventive and unique features associated with the closure assembly 10 include a snap-fit construction, which enables the production and assembly of the various components of the closure assembly 10 in a manner which eliminates or significantly reduces costly, time-consuming and/or overly complex production and assembly techniques.

Figure 1:
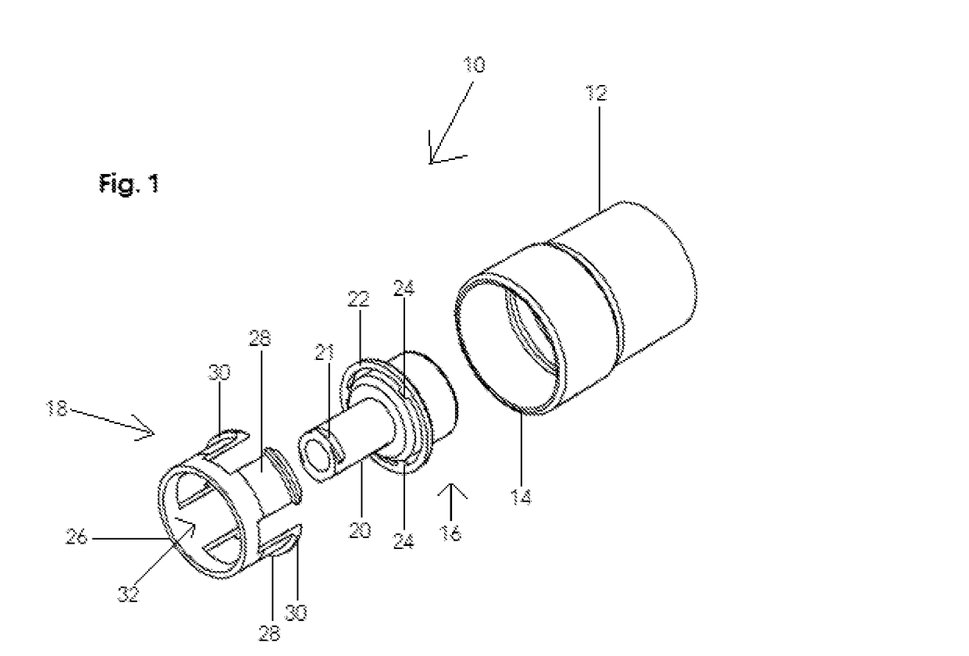
FIG. 1 is a perspective view in exploded form of a closure assembly according to the present invention in one preferred embodiment, and illustrated in an unassembled form.
Figure 2:
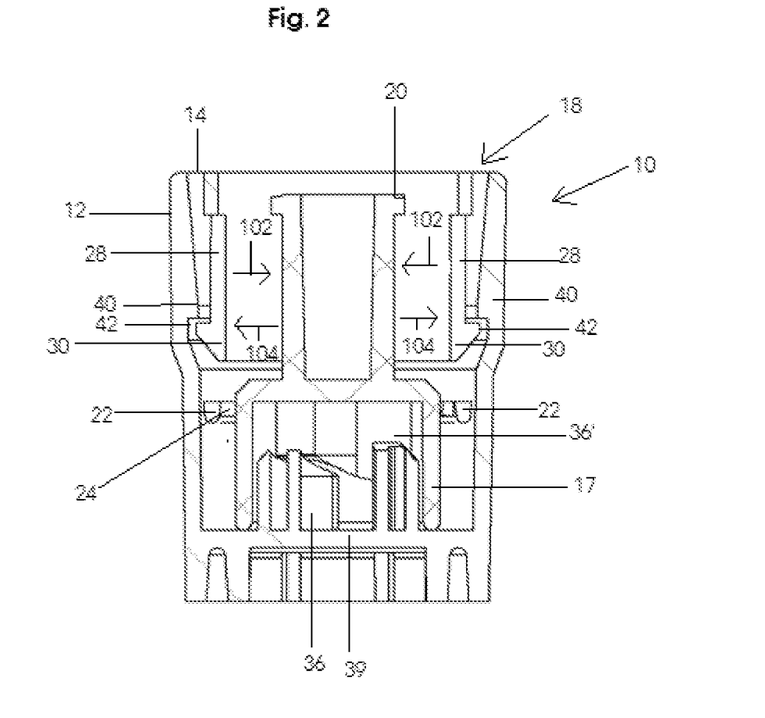
FIG. 2 is an interior sectional view of the embodiment of FIG. 1 in an assembled form.
Figure 3:
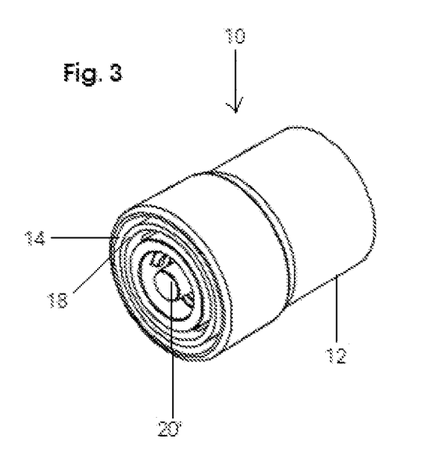
FIG. 3 is a perspective exterior view of the embodiment of FIGS. 1 and 2.
Figure 4:
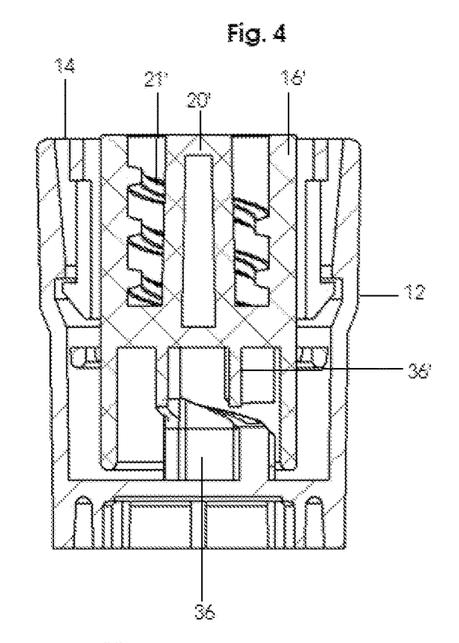
FIG. 4 is an interior sectional view of a closure assembly according to the present invention but illustrating another preferred embodiment.
Figure 5:
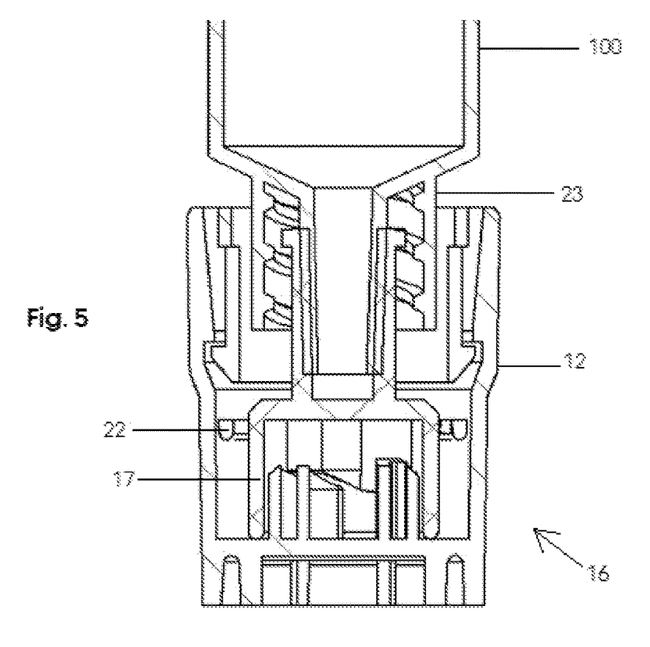
FIG. 5 is an interior sectional view in partial cutaway of the closure assembly of the embodiment of FIG. 1 being attached to a medical device in the form of a syringe.
Figure 6A:
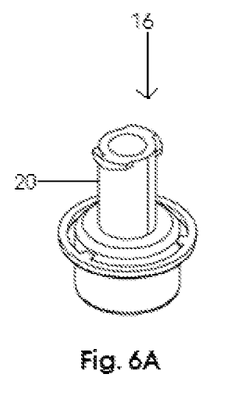
FIGS. 6A-6D are perspective views of a plurality of male and female tip caps, having an indicator member attached thereto, of the type which may be used in combination with the closure assembly of the present invention.
Figure 6B:
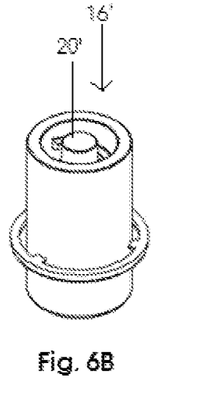
Figure 6C:
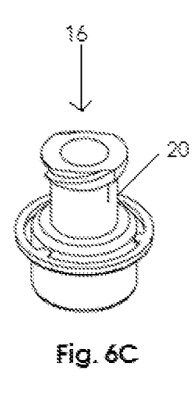
Figure 6D:
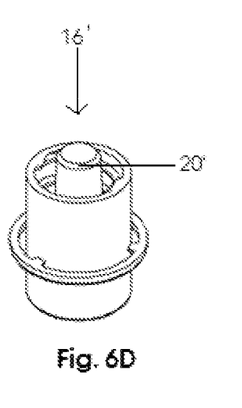
Figure 7A:
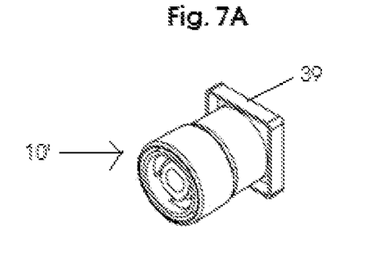
FIGS. 7A-7D are perspective views of a plurality of assembled closure assemblies which may include structural modifications which may be incorporated in the present invention.
Figure 7B:
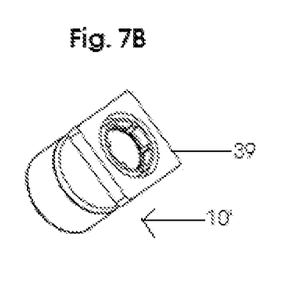
Figure 7C:
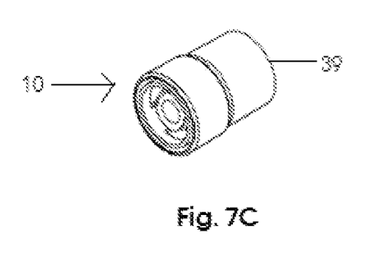
Figure 7D:
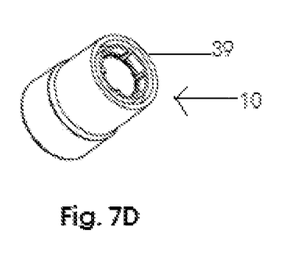

With initial reference to FIGS. 1-5, the closure assembly 10 includes a housing in the form of an outer sleeve 12 having an at least partially or substantially hollow interior, as represented in FIGS. 2, 4 and 5. Also, the sleeve 12 includes an open end 14 disposed in direct communication with the hollow interior of the sleeve 12. Further, the open end 14 and the hollow interior are cooperatively dimensioned to receive additional operative components, including a tip cap generally indicated as 16 and a retainer member generally indicated as 18, in an operative position therein.

More specifically, the tip cap 16 includes a flow restrictor 20 which has a male configuration including exterior threads 21 disposed to establish a threaded connection with the discharge end/or discharge port 23 of a medical device 100 such as a prefilled syringe, as clearly represented in FIG. 5. Additional features of the tip cap 16 include an indicator member 22 removably connected to an exterior of the tip cap 16 by at least one but preferably a plurality of frangible connectors 24. Moreover, in one or more embodiments of the closure assembly 10, the indicator member 22 is in the form of an indicator ring disposed in at least partially surrounding relation to a portion of the tip cap 16 to which it is attached.

As indicated, the closure assembly 10 also includes a retainer member 18 having a base 26 and at least one but preferably a plurality of flexible connectors 28 each in the form of a spring arm. As represented in at least FIGS. 1-5 the plurality of spring arms 28 are disposed outwardly from the base 26 in a common direction and are in spaced relation to one another. The spacing between the plurality of spring arms 28 facilitates the flexing thereof when inserted into the interior of the sleeve 12, as explained hereinafter. In addition, each of the one or more spring arms 28 includes a free or distal end 30 having an at least partially hook-like configuration which, along with the flexibility of the spring arms 28, facilitates the establishment of a snap-fit connection with interior surface portions 40,42 of the sleeve 12 as will be explained in greater detail with reference to at least FIG. 2.

As also represented, the retainer member 18 includes a substantially open interior 32 at least partially defined by the surrounding disposition of the base 26 and the plurality of spring arms 28. Such an open interior 32 allows the initial disposition of the flow restrictor 20 within the retainer member 18 in an accessible position relative to the open end 14. As represented in FIG. 5, such an accessible disposition of the flow restrictor 20 facilitates a connection with the discharge end 23 of the medical device/syringe 100, as the discharge end 23 passes at least partially through the open end 14 into the hollow interior of the sleeve 12.

As represented in FIGS. 1 and 2, the flow restrictor 20 has a female configuration for attachment to a cooperatively structured discharge end 23 of the syringe/medical device 100 to which it is to be attached. However, the versatility and structural features of the various components of the closure assembly 10 facilitate its use with both the female configured flow restrictor 20 of the tip cap 16, as well as a male configured flow restrictor 20' of the tip cap 16', as represented in FIGS. 3 and 4. However, the interconnection between the discharge end 23 of the medical device/syringe 100 and either the female or male flow restrictors, 20, 20' respectively, may be accomplished by a rotational, threaded connection as best represented in FIG. 5. Therefore, the sleeve 12 may also include a one-way drive assembly generally indicated as 36, such as a ramp and cliff drive assembly. The ramp and Cliff drive assembly 36 is integrally or fixedly connected to the interior of the sleeve 12 and may be cooperatively disposed and structured to interact with a corresponding one-way drive assembly 36' connected to a correspondingly disposed portion of the tip cap 16 or 16'.

With reference to FIGS. 6A-6D, the versatility of the various structural features of the closure assembly 10 or 10' allow its use with different types of female tip caps 16 or different types of male tip cap 16' which include appropriately configured female flow restrictors 20 and male flow restrictors 20'. As represented in FIGS. 7A-7D, different embodiments of the closure assembly 10 and/or 10' include the respective outer sleeve 12 having different structural configurations, including a round or circular closed end configuration 39 or a multi-sided, square or rectangular closed end 39'.

As emphasized herein, unique and inventive features of the closure assembly 10, 10', is the aforementioned "snap-fit" construction. Such snap-fit construction is at least partially defined by a snap-fit connection of the retainer member 18 on the interior of the sleeve 12 in a retaining engagement to the indicator member 22. In more specific terms, the retainer member 18 is disposed in its retaining position, as represented FIG. 2, by passing through the open end 14 of the sleeve 12. As the distal ends 30, or other portions of the spring arms 28, pass or slide over projecting portions 40 formed on the inner surface of the sleeve 12 they will flex inwardly, as indicated by directional arrow 102.

However, once the distal ends 30 pass beyond the inner projecting surface portion 40, the flexibility of each of the spring arms 28 will cause an outward flexing, as indicated by directional arrows 104. As a result, the distal ends 30, have a substantially hook-like configuration, which will "snap" into a receiving groove 42 disposed contiguous to the outwardly protruding surface portion 40, thereby defining a snap-fit connection therebetween. The cooperative structuring and configuring of the one or more spring arms 28 and the corresponding distal ends 30 with that of the protruding surface portion 40 and receiving grooves 42 will prevent or significantly restrict removal of the retainer member 18 from the interior of the sleeve 12, back through the open end 14.

As such, the retainer member 18 and in particular, the distal ends 30 of the spring arms 28 will be disposed in an interruptive, disconnecting disposition of the indicator member 22. Such a disconnecting engagement of the indicator member 22 with the one or more spring arms 28 will occur upon removal of the tip cap 16, 16' from the interior of the sleeve 12, through the open end 14, once the flow restrictor 20, 20' is connected to the discharge end 23 of the medical device/syringe 100.

Figure 8A:
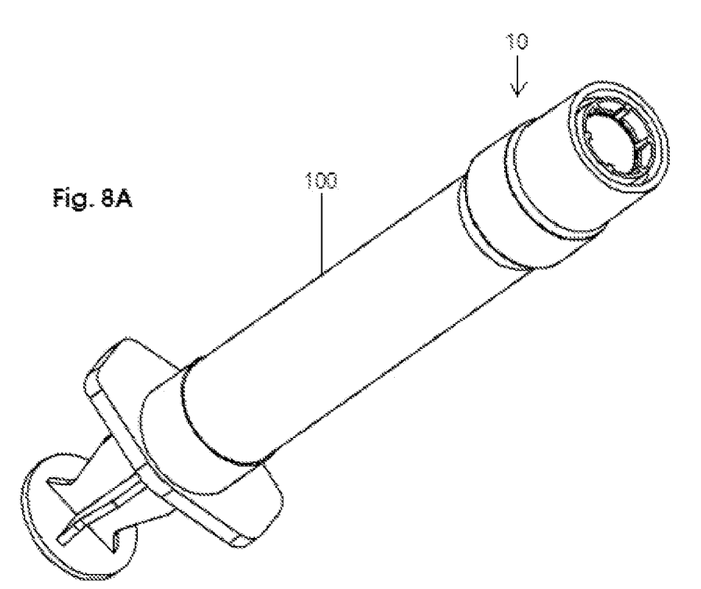
FIG. 8A is a perspective view of one embodiment of the closure assembly of the present invention connected in operative relation to a medical device in the form of a syringe.
Figure 8B:
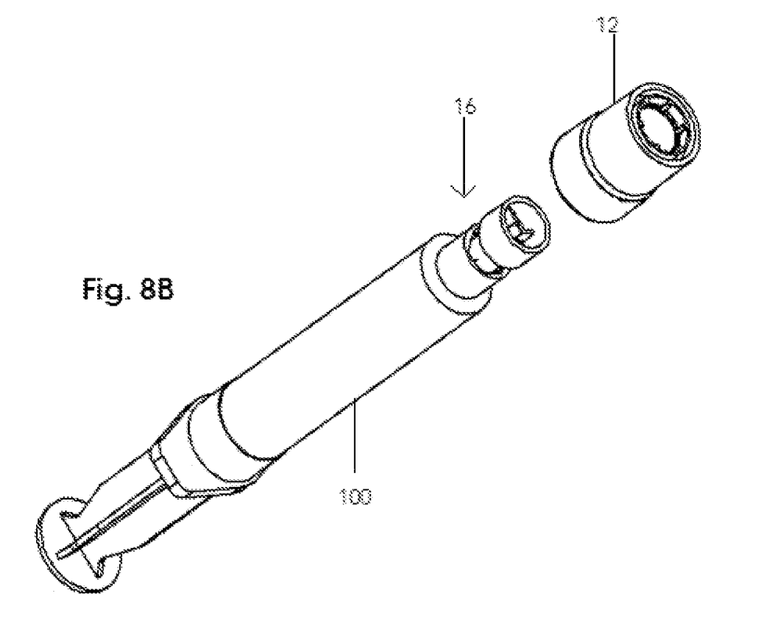
FIG. 8B is a perspective view in exploded form of the embodiment of FIG. 8A, wherein one embodiment of the closure assembly of the present invention is partially disconnected from the medical device.
Figure 9:
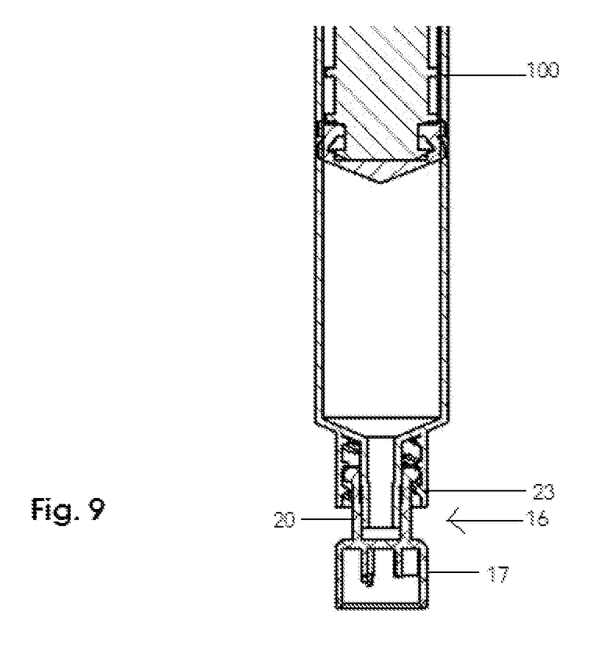
FIG. 9 is interior view in exploded partial section and partial cutaway, of the embodiment of FIG. 8B.

Accordingly, with reference to FIG. 8A, the syringe/medical device 100 is represented in its attached relation to the closure assembly 10. Upon the intended use (or tampering) of the medical device/syringe 100, the sleeve 12 is separated from the tip cap 16, as represented in FIG. 8B, by exerting an appropriately directed pulling force on either the sleeve 12 or the medical device/syringe 100 or both. Such a pulling force serves to separate the connected tip cap 16 from the sleeve 12 by forcing the tip cap 16 and flow restrictor 20 out through the open end 14, as represented in FIGS. 8B and 9. As should be apparent, the diameter or interior transverse dimension of the retainer member 18 is greater than that of the tip cap 16 including portion 17 thereof, as represented in FIG. 5. However, the diameter or internal transverse dimension of the retainer member 18 is smaller than that of the diameter or corresponding transverse dimension of the indicator member 22.

Therefore, the forced removal of the tip cap 16, including portion 17, will be accomplished by passage thereof through the open interior 32 of the retainer member 18 and open end 14. Concurrent to passage of the tip cap 16 into and through the open interior 32, the indicator member 22 will move with the tip cap 16 into the interruptive, disconnecting engagement with the one or more spring arms 28 and/or the distal ends 30 thereof. Such disconnecting engagement will result in a detachment of the indicator member 22, due to breakage of the frangible connectors 24, from the tip cap 16. Such a detachment of the indicator member 22 will further result in a capture of the indicator member 22 within the interior of the sleeve 12, as represented in FIG. 9, due to maintenance of the retainer member 18 in its retaining position after the tip cap 16 has been removed from the interior of the sleeve 12, as represented in FIG. 9.

Yet additional structural and operative features of the one or more embodiments of the present invention are represented in FIGS. 10-13. For purposes of clarity, the closure assembly is generally represented as 110, including a housing in the form of an outer sleeve 112, having an open end 14 and retainer member 18 disposed on the interior of the sleeve 112 in its retaining position. Further the tip cap 16 includes the flow restrictor 20' disposed in directly accessible relation to the opened and 14.

Structural modifications of the closure assembly 110 include the provision of an end cap 115 attached by a "snap-fit" connection to the sleeve 112 in substantially opposing relation to the open end 14. As such, the "snap-fit" connection of the end cap 115 to the sleeve 112 at least partially defines the "snap-fit" construction of the closure assembly 110. It is also emphasized that while some structural features, components, etc. of the closure assembly 110 differ from the closure assembly 10, 10' of the embodiments of FIGS. 1-9, the dimension, configuration, structure and operation of the retainer member 18 relative to the tip cap 16 and removably attached indicator member 22 are substantially equivalent.

Figure 10:
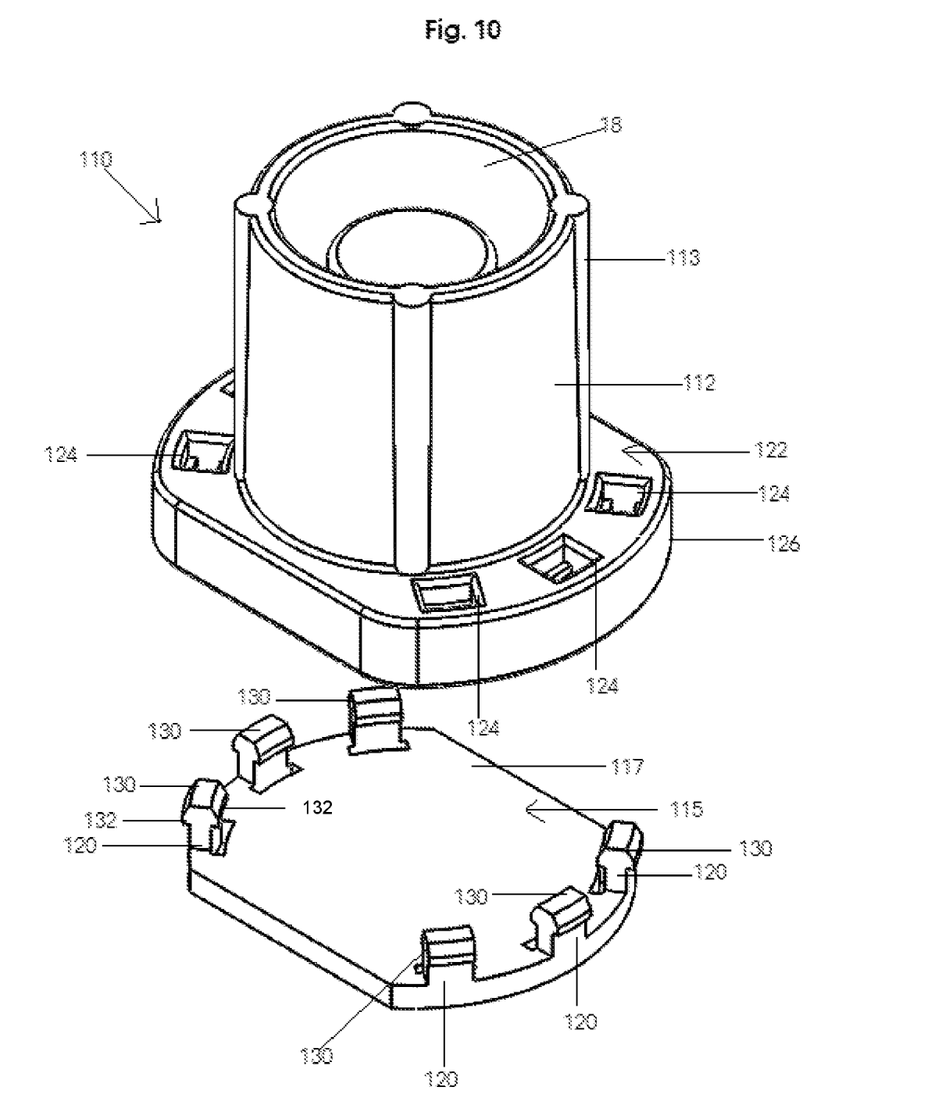
FIG. 10 is a perspective view in exploded form of yet another preferred embodiment of the closure assembly of the present invention.
Figure 11:
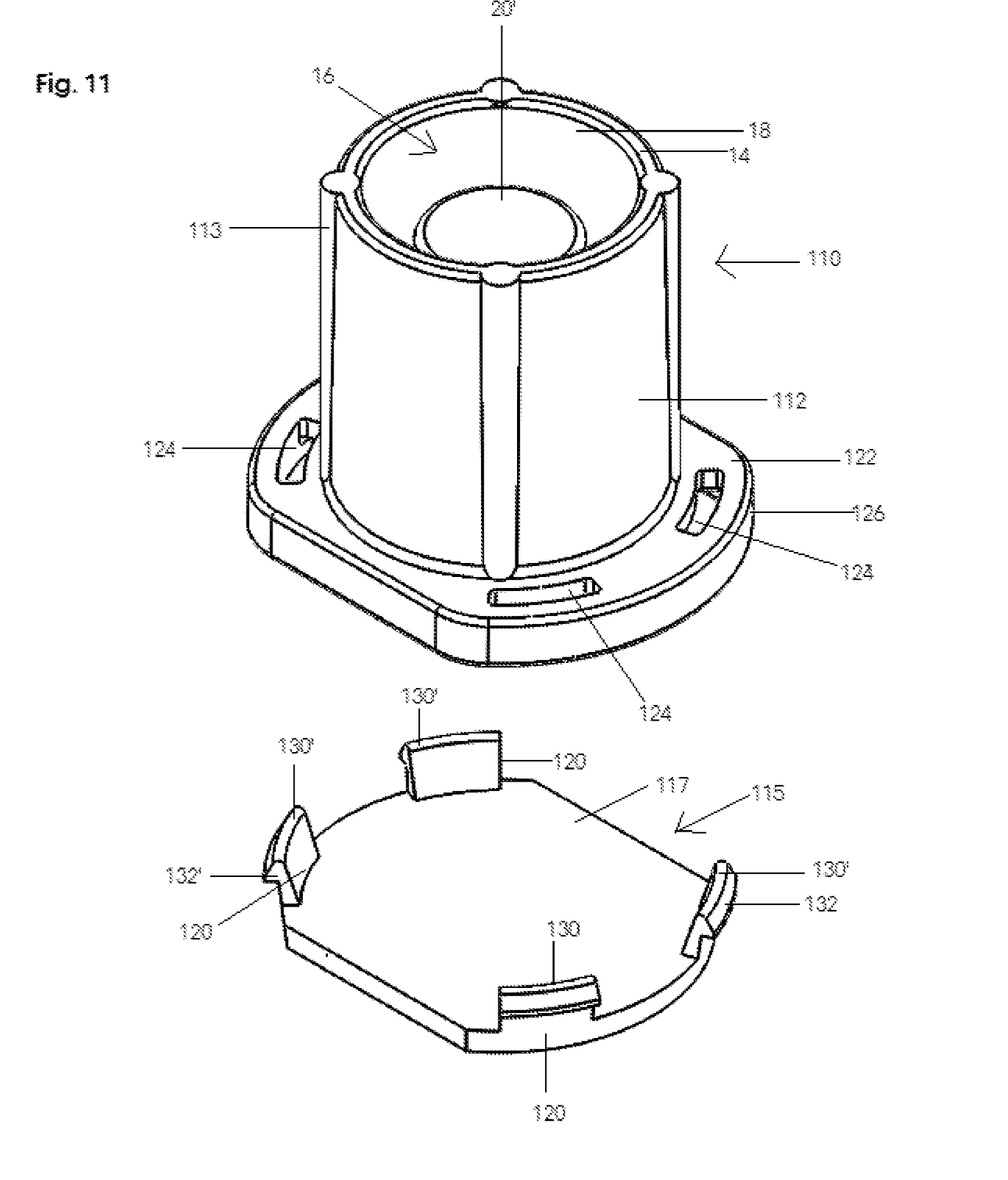
FIG. 11 is a perspective view in exploded form of yet another preferred embodiment of the closure assembly of the present invention.
Figure 12:
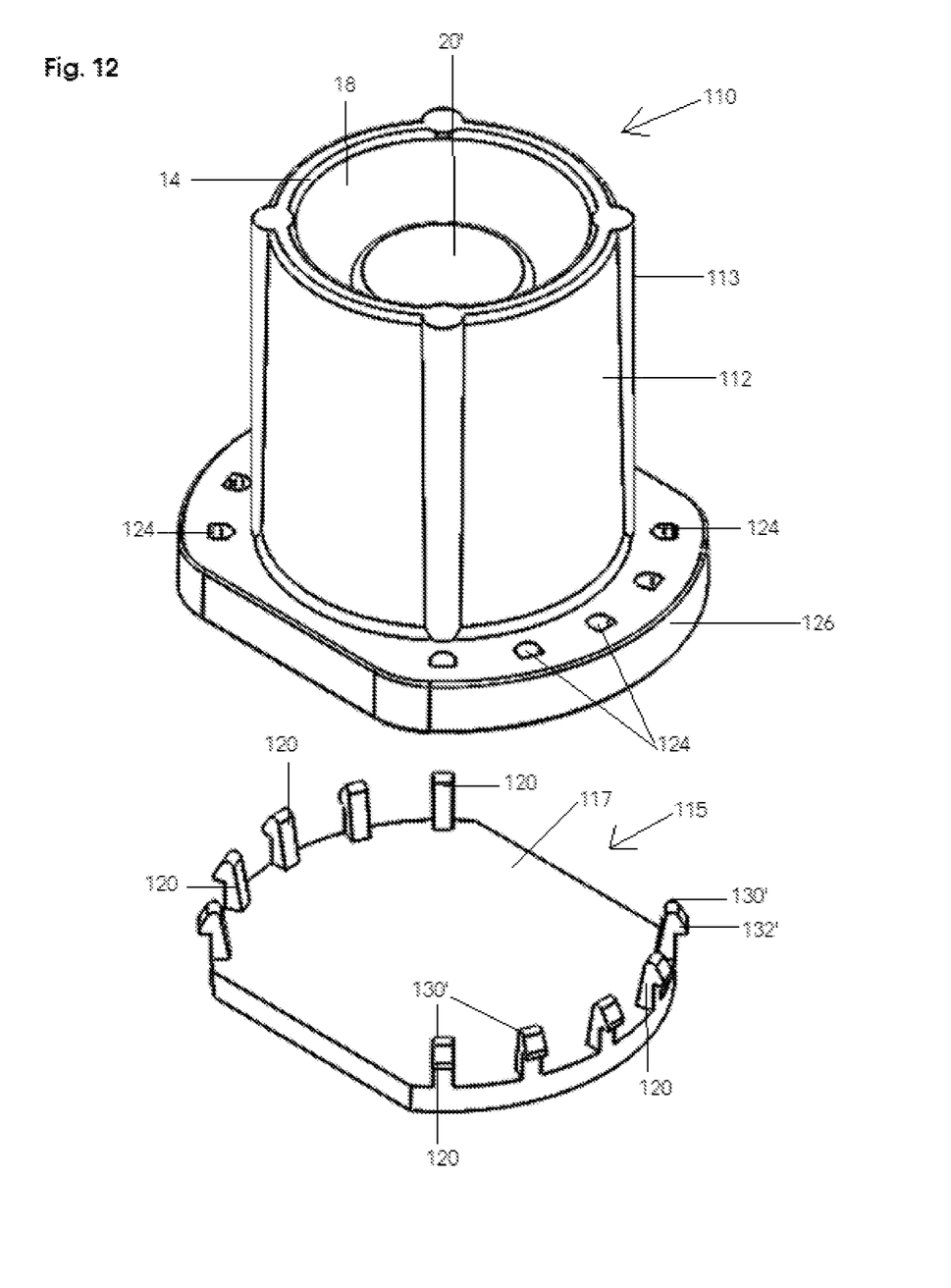
FIG. 12 is a perspective view in exploded form of yet another preferred embodiment of the closure assembly of the present invention.

Therefore, as represented in FIGS. 10-12 the end cap 115 includes a base 117 and at least one, but preferably a plurality of outwardly extending spring fingers 120, attached thereto. Further, the sleeve 112 includes an apertured construction generally indicated as 122 defined by at least one, but preferably a plurality of apertures 124 formed in a radially outward extending flange 126 integrally or otherwise fixedly secured to the sleeve 112. In addition, each of the spring fingers 120 includes an outer or free 130 having a hook-like configuration, as represented. In the embodiment of FIG. 10, the hook-like configuration of the free ends 130 of each of the one or more spring figure 20 may have a "double-hook" configuration at least partially defined by two spaced apart hook segments 132 formed on opposite sides of the corresponding spring FIG. 120.

In cooperation therewith, the one or more apertures 124 are cooperatively structured and configured with at least the free ends 130 of each of the spring figures 120 to establish a snap-fit connection therewith. The snap-fit connection is established by penetration of each of the plurality of spring figures 120 into the flange 126 through a different one of the apertures 124. The flexibility of each of the spring fingers 120 as well as the configuration of the free ends 130 thereof facilitate the penetration of each of the free ends 130 into a corresponding aperture 124 and a "snap-fit" locking engagement therewith. As a result of such locking, snap-fit engagement, the end plate 115 will not be removable from its closing relation to the interior of the sleeve 112, to which it is attached, absent a breakage, damage or malfunction of the spring fingers 120 and/or apertures 124.

Figure 13:
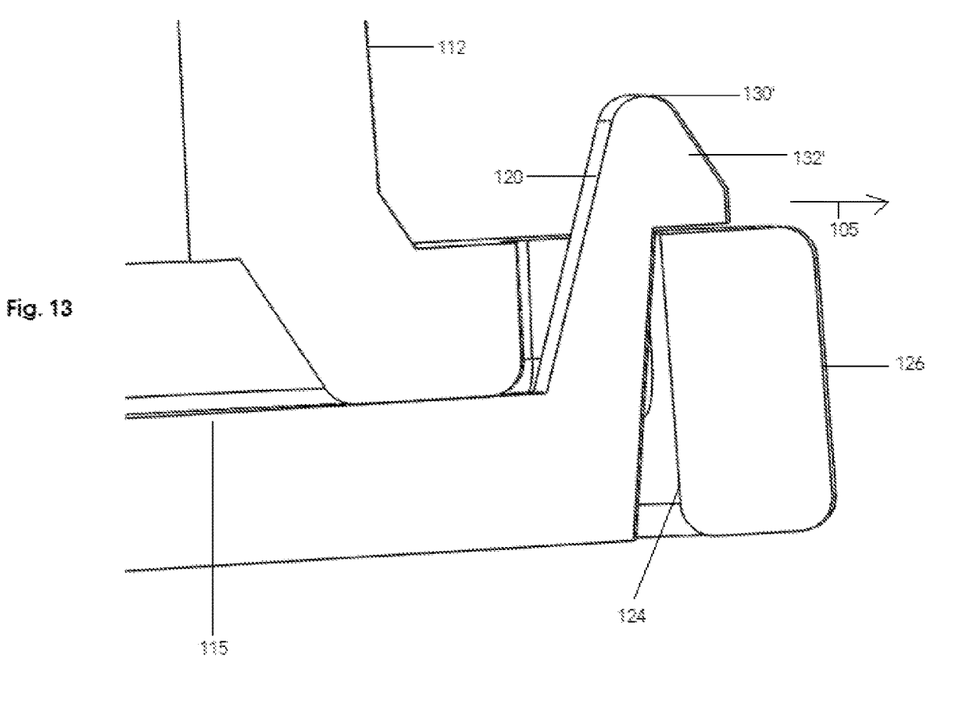
FIG. 13 is a perspective cutaway view in detail of a "snap-fit" connection of the embodiments of at least FIGS. 11 and 12.

A comparison of the embodiment of FIG. 10 with that of FIGS. 11-13 provide an indication that the spring fingers 120 may vary in number, structure and configuration. More specifically, the spring fingers 120 in the embodiment of FIGS. 11, 12 and 13 include distal ends 130' having a single hook-like configuration at least partially defined by a single hook segment 132'. As such, the apertured construction, generally indicated as 122, of the sleeve 112 comprise one or more apertures 124, corresponding in number to that of the one or more spring fingers 120. Moreover, the plurality of apertures 124 defining the apertured construction 122 of the embodiments of FIGS. 11-13 are cooperatively structured to define and facilitate the "snap-fit" connection with the plurality of spring fingers 120, having a single hook configuration comprising a single hook segment 132'.

With reference to the detailed representation of FIG. 13, each of the spring fingers 120 have a flexible construction enabling the passage thereof through a correspondingly disposed aperture 124. As the spring finger 120 passes into and through the corresponding aperture 124, the flexibility thereof will cause an outwardly biased "snap" movement of the free end 130' as represented by directional arrow 105. This outwardly biased snap movement establishes a "snap-fit" connection of the single hook segment 132' with the outer periphery surrounding a corresponding aperture 124, as represented.

Another structural and operative feature included in each of the embodiments of FIGS. 10-12 is the provision of a plurality of ribs 113 extending or protruding outwardly from the exterior surface of the sleeve 112, in spaced relation to one another. The plurality of ribs 113 facilitate the gripping and/or handling of the closure assembly 110 especially, but not exclusively, during an attempted rotation or other manipulation of the sleeve 112 as the tip cap 16 is being connected to the discharge end 23 of the medical device/ syringe 100.

Accordingly, the snap-fit construction of the closure assembly 10, 10', 110, etc. enables the elimination or significant reduction of certain production and assembly techniques, at least some of which involve ultrasound welding, commonly found in known or conventional closures of this type.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly for a medical device comprising:
    an outer sleeve including an at least partially hollow interior,
    said outer sleeve including an open end disposed in communicating relation to said hollow interior,
    a tip cap including a flow restrictor disposed within said hollow interior in accessible relation to said open end,
    an indicator member removably connected to said tip cap within said outer sleeve,
    a retainer member structured to define a non-removable, yet movable snap-fit connection of said retainer member with an interior surface of said outer sleeve,
    said retainer member disposed within said outer sleeve in an interruptive, disconnecting relation to said indicator member,
    said indicator member and said tip cap disposed within said outer sleeve in unattached, spaced relation to said retainer member;
    said indicator member movable with said tip cap within said outer sleeve, relative to said retainer member and into retained, disconnecting engagement with said retainer member, concurrent to removal of said tip cap from said outer sleeve, and
    said indicator member captured within said hollow interior upon removal of said tip cap from said sleeve through said open end.

2. The closure assembly as recited in claim 1 wherein said retainer member is disposed exteriorly, in non-interruptive engagement with said tip cap, upon removal of said tip cap from said outer sleeve, through said open end.

3. The closure assembly as recited in claim 1 wherein said retainer member includes an open interior dimensioned to receive said tip cap therein, upon removal of said tip cap from said outer sleeve, through said open end.

4. The closure assembly as recited in claim 3 wherein said flow restrictor is disposed within said open interior, in accessible relation to the medical device, through said open end.

5. The closure assembly as recited in claim 1 wherein said non-removable snap-fit connection comprises a rotationally movable engagement of said retainer member with said interior surface.

6. The closure assembly as recited in claim 1 wherein said retainer member comprises a base and at least one connector attached thereto, said at least one connector comprising a flexible construction disposed and structured to define said non-removable snap-fit connection with said interior surface.

7. The closure assembly as recited in claim 6 wherein said at least one connector comprises a spring arm movably connected to said base and disposed in a non-removable snap-fit engagement with said interior surface.

8. The closure assembly as recited in claim 7 wherein said spring arm comprises a distal end cooperatively structured with said interior surface to define said non-removable, snap-fit engagement with said interior surface.

9. The closure assembly as recited in claim 7 wherein said retainer member comprises a plurality of spring arms connected to said base, in spaced relation to one another, each of said plurality of spring arms disposed in non-removable, snap-fit engagement with said interior surface of said outer sleeve.

10. The closure assembly as recited in claim 9 wherein said base comprises a substantially annular configuration having an open interior, each of said plurality of spring arms depending outwardly from said base in collectively surrounding relation to said flow restrictor on the interior surface of said outer sleeve.

11. The closure assembly as recited in claim 1 wherein said outer sleeve further includes a closed end comprising an end cap attached to said outer sleeve by a snap-fit connection.

12. The closure assembly as recited in claim 11 wherein said end cap includes at least one spring-finger disposed in non-removable, penetrating engagement with said outer sleeve.

13. The closure assembly as recited in claim 12 wherein said outer sleeve includes an apertured construction including at least one aperture disposed and configured to receive said at least one spring-finger therein to collectively define said snap-fit connection of said end cap to said outer sleeve.

14. The closure assembly as recited in claim 12 wherein said at least one spring-finger comprises a distal end including at least a single-hook configuration.

15. The closure assembly as recited in claim 11 wherein said outer sleeve includes an apertured construction including a plurality of apertures, said end cap including a plurality of spring fingers each disposed in non-removable, penetrating engagement with said outer sleeve, through a different one of said plurality of apertures, said plurality of spring fingers and said plurality of apertures cooperatively structured to collectively define said snap-fit connection of said end cap to said outer sleeve.

16. A closure assembly for a medical device comprising:
an outer sleeve including an at least partially hollow interior,
said outer sleeve including an open end disposed in communicating relation to said hollow interior,
a tip cap including a flow restrictor disposed within said hollow interior in accessible relation to said open end,
an indicator member removably connected to said tip cap within said outer sleeve,
a retainer member inserted within said outer sleeve and structured to define a snap-fit connection of said retainer member to an interior of said outer sleeve,
said retainer member disposed within said outer sleeve in an interruptive, disconnecting relation to said indicator member,
said indicator member and said tip cap disposed within said outer sleeve in unattached, spaced relation to said retainer member;
said indicator member movable with said tip cap within said outer sleeve, relative to said retainer member and into retained, disconnecting engagement with said retainer member, concurrent to removal of said tip cap from said outer sleeve, and
said indicator member captured within said hollow interior upon removal of said tip cap from said sleeve through said open end.

17. A closure assembly for a medical device comprising:
an outer sleeve including an at least partially hollow interior,
said outer sleeve including an open end disposed in communicating relation to said hollow interior,
a tip cap including a flow restrictor disposed within said hollow interior in accessible relation to said open end,
an indicator member removably connected to said tip cap within said outer sleeve,
a retainer member cooperatively structured with said outer sleeve to define a snap-fit connection of said retainer member to an interior surface of said outer sleeve,
said retainer member disposed within said outer sleeve in an interruptive, disconnecting relation to said indicator member,
said indicator member and said tip cap disposed within said outer sleeve in unattached, spaced relation to said retainer member;
said indicator member movable with said tip cap within said outer sleeve, relative to said retainer member and into retained, disconnecting engagement with said retainer member, concurrent to removal of said tip cap from said outer sleeve, and
said indicator member captured within said hollow interior upon removal of said tip cap from said sleeve through said open end.

\* \* \* \* \*